United States Patent
Phillips

(10) Patent No.: US 7,338,447 B2
(45) Date of Patent: Mar. 4, 2008

(54) BLOOD FLOW OXYGEN MEASUREMENT SYSTEM AND METHOD

(75) Inventor: Robert Allan Phillips, Coffs Harbour (AU)

(73) Assignee: USCOM Pty Ltd, Korora, New South Wales (AU)

( * ) Notice: Subject to any disclaimer, the term of this patent is extended or adjusted under 35 U.S.C. 154(b) by 222 days.

(21) Appl. No.: 10/513,632

(22) PCT Filed: May 5, 2003

(86) PCT No.: PCT/AU03/00526

§ 371 (c)(1), (2), (4) Date: Nov. 5, 2004

(87) PCT Pub. No.: WO03/092491

PCT Pub. Date: Nov. 13, 2003

(65) Prior Publication Data

US 2005/0187469 A1 Aug. 25, 2005

(30) Foreign Application Priority Data

May 6, 2002 (AU) .................................. PS2145

(51) Int. Cl.
*A61B 8/14* (2006.01)
(52) U.S. Cl. .................................................. 600/438
(58) Field of Classification Search ........ 600/437–438, 600/453–457, 459, 465, 468, 323–324, 479, 600/483, 500–502, 504–507

See application file for complete search history.

(56) References Cited

U.S. PATENT DOCUMENTS

| | | | |
|---|---|---|---|
| 3,675,640 A * | 7/1972 | Gatts | 600/484 |
| 3,980,075 A | 9/1976 | Heule | |
| 4,509,526 A * | 4/1985 | Barnes et al. | 600/456 |
| 4,671,295 A * | 6/1987 | Abrams et al. | 600/463 |
| 4,867,165 A | 9/1989 | Noller et al. | |
| 5,020,516 A * | 6/1991 | Biondi et al. | 601/44 |
| 5,152,291 A * | 10/1992 | Dias | 600/454 |
| 5,265,615 A * | 11/1993 | Frank et al. | 600/485 |
| 5,361,771 A * | 11/1994 | Craine et al. | 600/532 |
| 5,389,217 A | 2/1995 | Singer | |
| 6,234,963 B1 * | 5/2001 | Blike et al. | 600/300 |
| 6,292,689 B1 * | 9/2001 | Wallace et al. | 600/547 |
| 6,315,730 B1 | 11/2001 | Hoff et al. | |
| 6,468,219 B1 * | 10/2002 | Njemanze | 600/454 |
| 7,192,403 B2 * | 3/2007 | Russell | 600/504 |

FOREIGN PATENT DOCUMENTS

GB 1 461 345 1/1977

\* cited by examiner

*Primary Examiner*—Francis J. Jaworski
(74) *Attorney, Agent, or Firm*—Merchant & Gould P.C.

(57) ABSTRACT

An apparatus for measuring physiologic tissues perfusion information including: a first device producing a first output indicative of blood flow of a patient; a second device producing a second output indicative of oxygen content of the blood; and a processor combining said first and said second outputs to produce a third output indicative of tissue perefusion.

17 Claims, 5 Drawing Sheets

BLOOD FLOW OXYGEN MEASUREMENT SYSTEM AND METHOD

FIELD OF THE INVENTION

This invention relates to measurement and monitoring of vital physiological tissue perfusion information.

BACKGROUND OF THE INVENTION

Tissues requires oxygen for life and this is supplied by the stream of blood which transports dissolved oxygen to the cells. The amount of oxygen reaching the tissues is a function of the volume of blood pumped by the heart and the oxygen content of the blood. Hereto before there has been no device producing a single output indicative of tissue perfusion and no ready measure for correlating a reading of tissue perfusion with the presence or absence of a condition within a patient.

SUMMARY OF THE INVENTION

It is an object of the present invention to provide an improved blood oxygen measurement method and apparatus.

In a first aspect of the preset invention there is provided an apparatus for measuring physiologic tissues perfusion information including:

a first device producing a first output indicative of blood flow of a patient;

a second device producing a second output indicative of oxygen content of the blood; and a processor combining said first and said second outputs to produce a third output indicative of tissue perfusion.

In a preferred embodiment, the fist device uses a CW Doppler method to measure blood flow. The second device can use oximetry to measure oxygen content.

In a preferred embodiment the third output is indicative of at least one of percent distance (stroke saturation), percent minute distance (saturation output), percent.

In a preferred embodiment the third output is indicative of at least one of percent distance (stroke saturation), percent minute distance (saturation output), percent stroke volume (saturation stroke volume) and percent output (saturation output).

In a preferred embodiment, the apparatus combines intro cardiac or aortic flow with peripheral oximetry.

In a second aspect, the invention provides a method of measuring physiologic tissue perfusion information including obtaining a measurement of blood flow and a measurement of blood oxygen content, and combining said measurements to produce an output indicative of tissue perfusion.

In a further aspect, the invention provides a method of creating a tissue perfusion index including:

(a) obtaining a measurement of blood flow and a measurement of blood oxygen content from a patient;

(b) combining said measurements to calculate a parameter indicative of tissue perfusion in said patient;

(c) repeating steps (a) and (b) on a plurality of patients to obtain a set of calculations of said parameter for said plurality of patients;

(d) processing the set of calculated parameters to obtain a statistically averaged index of said parameter for a population.

In a further aspect, the invention provides a method of creating a tissue perfusion index for a healthy population including:

(a) obtaining a measurement of blood flow and a measurement of blood oxygen content from a healthy patient;

(b) combining said measurements to calculate a parameter indicative of tissue perfusion in said healthy patient;

(c) repeating steps (a) and (b) on a plurality of healthy patients to obtain a set of calculations of said parameter for said plurality of patients;

(d) processing the set of calculated parameters to obtain a statistically averaged index of said parameter for a healthy population, In a further aspect, the invention provides a method of creating a systemic perfusion index for a population with a known condition including:

(a) obtaining a measurement of blood flow and a measurement of blood oxygen content from a patient with said known condition;

(b) combining said measurements to calculate a parameter indicative of tissue perfusion in said patient;

(c) repeating steps (a) and (b) on a plurality of patients with said known condition to obtain a set of calculations of said parameter for said plurality of patients;

(d) processing the set of calculated parameters to obtain a statistically averaged index of said parameter for a population with said known condition.

In a further aspect, the invention provides a method of diagnosing a condition in a patient including:

(a) obtaining a measurement of blood flow and a measurement of blood oxygen content from a patient;

(b) combining said measurements to calculate a parameter indicative of tissue perfusion in said patient;

(c) comparing said calculated parameter with a statistically averaged index of said parameter to determine the extent to which said condition exists within said patient

BRIEF DESCRIPTION OF THE DRAWINGS

The invention will now be described by way of example only with reference to preferred embodiments and to the accompanying figures in which.

DETAILED DESCRIPTION OF PREFERRED EMBODIMENTS

Figure 1:
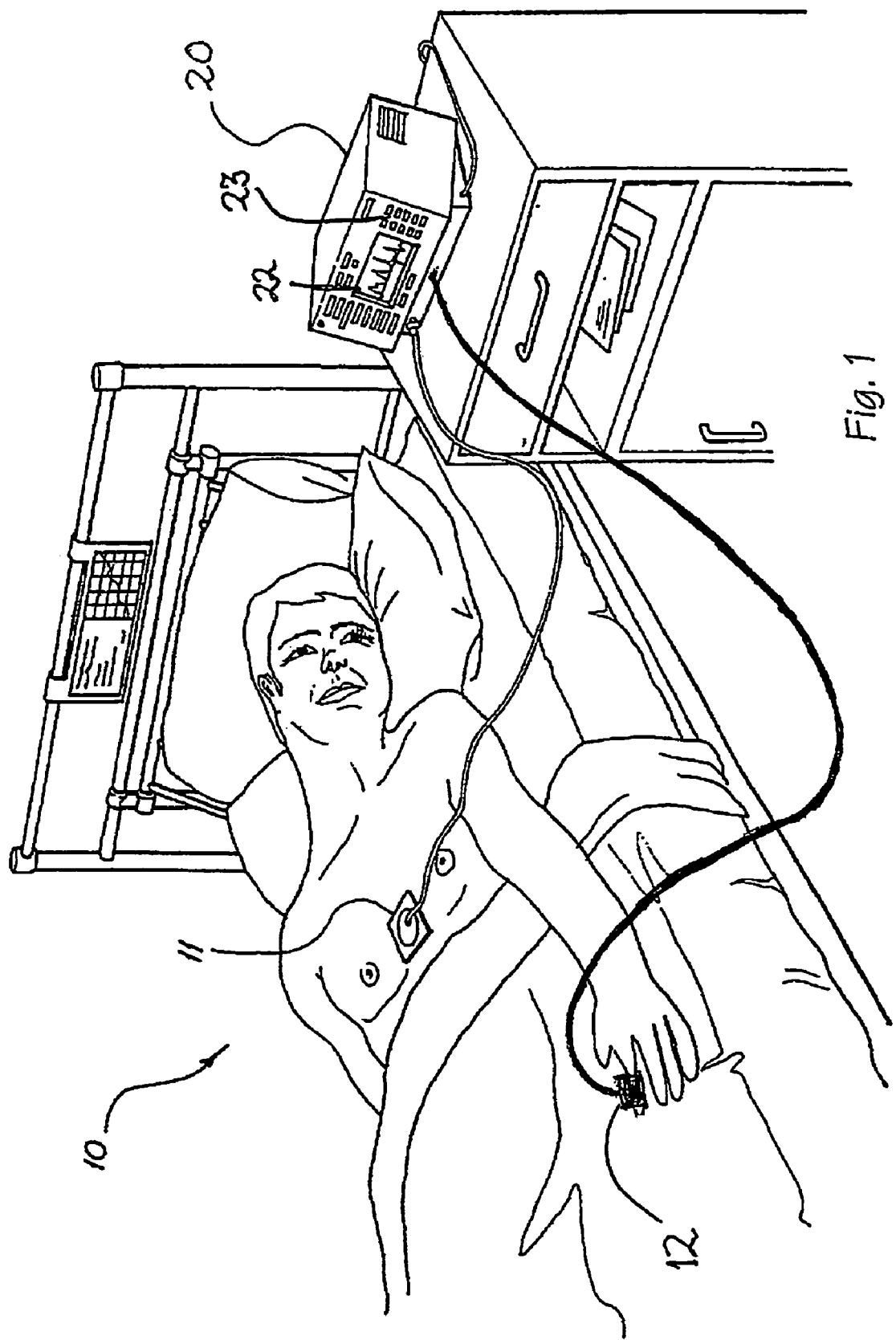
FIG. 1 shows an apparatus of a preferred embodiment connected to a patient.

Referring to FIG. 1 there is shown a patient 10 to which is attached an apparatus in accordance with a preferred embodiment of the invention. The apparatus 10 includes a non-invasive blood flow monitor 11 and digital oximetry device 12.

The outputs of the blood flow 11 and the oximetry 12 devices are combined in a processor unit 20 which may be located adjacent the patient. The processor unit 20 includes a processor (internal) and display screen 22. Control keys 23 on the outside of the processor unit 20 can be used to select one or more tissue perfusion parameters to be calculated and displayed on the screen 22 as will be described in greater detail below. The processor unit may also receive inputs from external devices (not shown) such as a heart rate monitor and may also receive inputs entered manually by a user using control keys 23. Further, the processor unit can be in turn interconnected to a computer network for the transfer of information to and from the processor unit 20.

Figure 2:
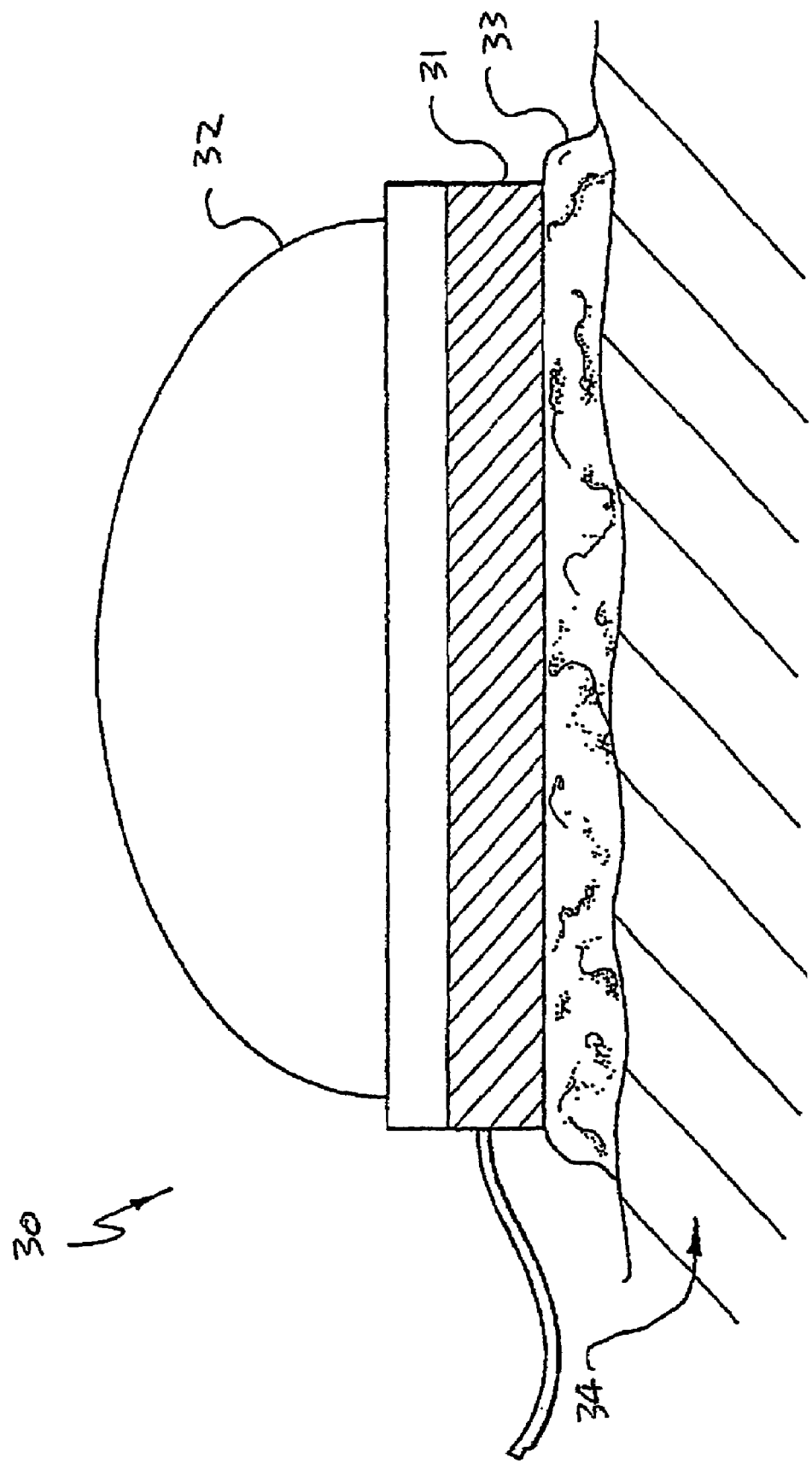
FIG. 2 shows an ultrasonic device for measuring blood flow.

FIG. 2 shows an example of an actuator for attachment to the skin surface. Ideally CW Doppler is utilised to monitor blood flow. CW Doppler is a non-invasive technique in which ultrasonic signals from transducer elements are directed into a blood carrying vessel of a patient. Doppler shifts in the reflected signal provide an indication of the rate of blood flow. In FIG. 2, a transducer element 30 includes an ultrasonic transducer 31 attached to a positioning device 32 which can be used to initially set the position of the transducer. Between the transducer 31 and a patient's skin 34 is placed a gel coupling layer 33 for coupling the ultrasonic transducer vibrations to the skin 34. The principles of CW Doppler flow measurement are known and do not themselves form part of the present invention Patent Cooperation Treaty (PCT) publication number WO 99/66835 to the present assignee, the contents of which are incorporated herein by cross-reference, described in more detail an ultrasonic transducer device suitable for measuring blood flow using the CW Doppler method. In the embodiment shown in FIG. 1, the transducer elements are placed on the patient to obtain intra-cardiac or aortic signals, for example through the suprasternal notch.

Figure 3:
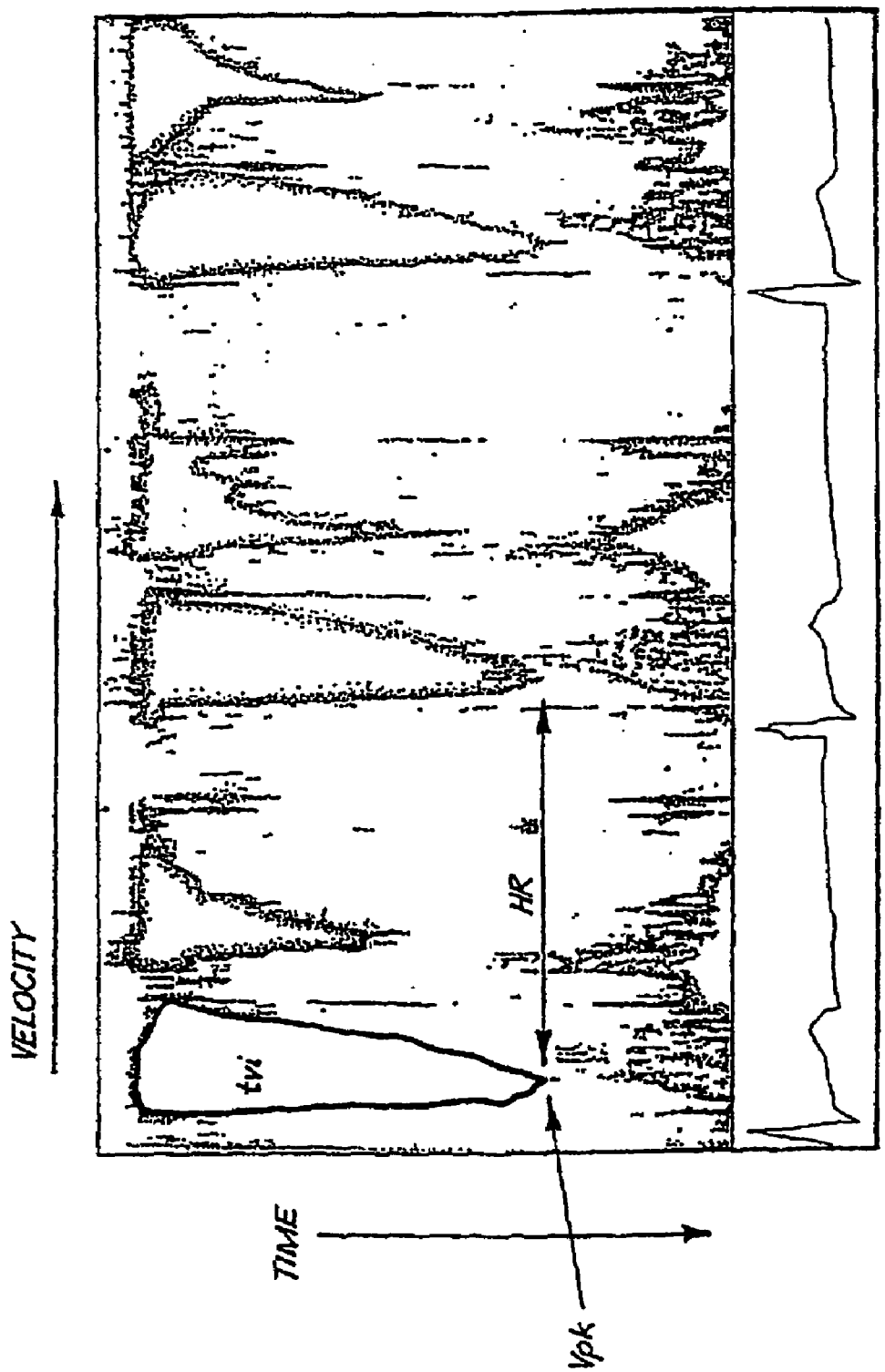
FIG. 3 shows an output from the device of FIG. 2.

The CW method detects the velocity of individual blood cells by measuring the frequency change of a reflected ultrasound beam and displaying this as a time velocity flow profile, an example of which is shown in FIG. 3. The transducer output forms an input to the processor unit 20. From the velocity time flow profile, the processor can calculate a velocity time integral (vti) and other relevant information such as heart rate (HR), and peak velocity, each of which is shown in FIG. 3.

Oximetry is a known method of measuring the oxygen saturation ($O_2$) of blood. Latest transcutaneous oximetry devices using infra-red technology are made non-invasive and of small size. Examples include U.S. Pat. Nos. 6,553,241, 6,542,764, 2,706,927, 5,632,272. In the embodiment shown in FIG. 1, digital oximetry is used to obtain an oxygen concentration reading from a patient's finger. Persons skilled in the art are aware of adequate display drivers, displays, transducer drivers and transducers to utilise in view of the disclosures herein.

The processor unit receives the outputs of the blood flow monitor and the oximetry device. Heart rate may also be input into the processor from a separate heart rate monitor. Alternatively, the heart rate may be calculated from analysis of the blood flow profile, e.g. by counting the number of beat peaks over a period of time.

The processor mathematically combines its inputs to derive new parameters pertaining to tissue perfusion. A first derived measure it the percent distance stroke saturation (SS) and is a function of the oxygen saturation ($O_2$) and the stroke distance measured as the velocity time integral (vti) of the blood flow profile over a single stroke:

$$SS = O_2 \times vti$$

The percent minute distance saturation output (SO) can is a function of oxygen saturation, stroke distance and heart rate (HR);

$$SS = O_2 \times vti \times HR.$$

Percent stroke volume (saturation stroke volume SSV) is a function of oxygen saturation, the time velocity integral from the blood flow profile and the Doppler flow profile cross sectional area (XSA) and can be calculated as follows:

$$SS = O_2 \times vti \times XSA.$$

Percent stroke volume describes the volume of oxygen passing through body tissue per heartbeat.

Percent output (saturation output) is a function of oxygen saturation, the time velocity integral from the blood flow profile, the Doppler flow profile cross sectional area and the heat rate:

$$SSV = O_2 \times tvi \times XSA \times HR.$$

Percent output describes the total volume of oxygen passing through the body tissue.

Analysis based on these new tissue perfusion parameters provide for an improved understanding of physiology and pathophysiology associated with cardiovascular function, exercise and pulmonary function. They can also facilitate new methods of categorising conditions and new methods of diagnosing conditions within a patient. Furthermore, these new parameters can also provide greater monitoring of conditions within a patient, e.g. during recovery, as the parameters can provide complete indications of tissue perfusion which relates directly to the ongoing health of the tissue.

The above benefits may be realised by the creation of issue perfusion indices. For example, a tissue perfusion parameter produced by the combination of blood flow and oxygen concentration readings may be measured for a plurality of known healthy patients to determine an index for the parameter, which index denotes good health. The perfusion index can be established by measuring the parameter in a plurality of healthy patients and then statistically averaging the results to determine a value or range of values of the tissue perfusion parameter.

Similarly, the same parameter may be measured in a plurality of patients having a known condition to obtain a tissue perfusion index relating to that parameter, which index describes the presence of that condition.

Diagnosis of a condition in a patient can then be performed by calculating the parameter for the patient and comparing the result with the parameter indices to determine whether the condition exists in the patient.

Statistical averaging of the parameter values of individual patients may take into account such variables as age, sex, height, weight, ethnicity etc. The indices thereby produced may be scaled according to these factors, e.g. the upper and lower limits of a tissue perfusion parameter denoting good health may vary with age or there may be a different range of values depending on sex.

As the processor unit is able to perform a real time calculation of a tissue perfusion parameter, the preferred embodiment of the present invention allows for continuous monitoring and healthcare of a patient based on the tissue perfusion reading. For example, a patient in recovery may have tissue perfusion monitored in a relevant region of the body. If the tissue perfusion reaches a healthy range of the tissue perfusion index, then good health is indicated and treatment may be ceased or reduced. Conversely, the tissue perfusion reading of a patient may change to a healthy level. An alarm state may be triggered when the tissue perfusion reading crosses a threshold level so that corrective action, e.g. to the course of treatment, may be taken.

Figure 4:
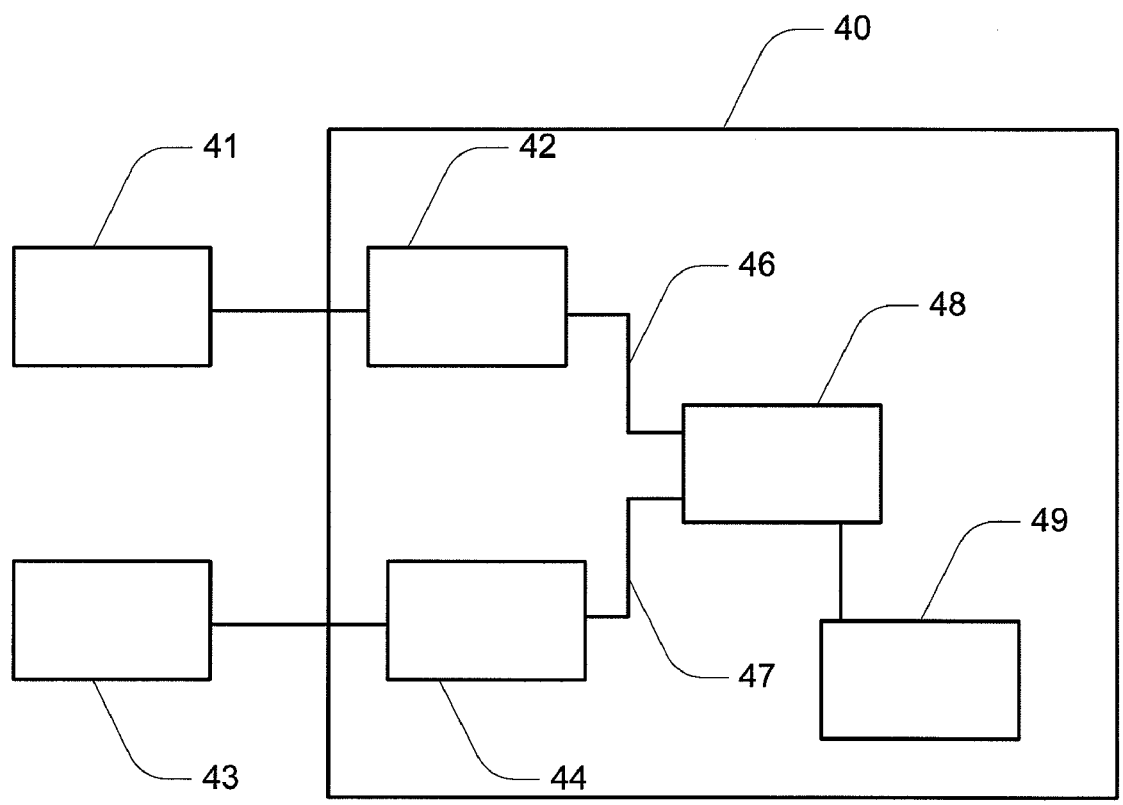
FIG. 4 is a schematic of the signal processing aspects of the apparatus.

FIG. 4 shows, in functional block diagram from, one form of construction of the signal processing aspects of the apparatus. It will be evident to those skilled in the art of complex electronic system design that a hardware implementation of the preferred embodiment can take many different forms from standard programmed microprocessor or microprocessor arrangements to more customised arrangements including Field Programmable Gate Arrays (FPGAs) or dedicated Application Specific Integrated Circuits (ASICs).

Output from the CW transducer 41 is passed to a first pre-processor 42 within the processing unit 40. The CW transducer output is edge extracted and image processed using known techniques. The pre-processor determines the relevant flow parameters, e.g. the flow profile, time velocity integral, heart rate etc. The flow parameters may be calculated over successive frames, i.e. heartbeats, either to obtain average readings, or to determine variations in time based parameters.

Simultaneously, the oximetry device 43 response is provided to a second pre-processor 44 and processed to determine an oxygen concentration value.

The respective outputs 46, 47 of the first and second pre-processors are then combined at the main processor 48 to calculate a tissue perfusion parameter, for example of the type described above. The tissue perfusion parameter may be compared with a tissue perfusion index stored in memory 49, prior to the parameter value, index values and other relevant information, e.g. whether an alarm condition exists, being displayed on the screen of the processor unit.

If necessary, either preprocessor 42, 44 or the main processor 48 may receive inputs from external devices, e.g. a heart rate monitor if heart rate is not calculated directly from the blood flow profile.

Figure 5:
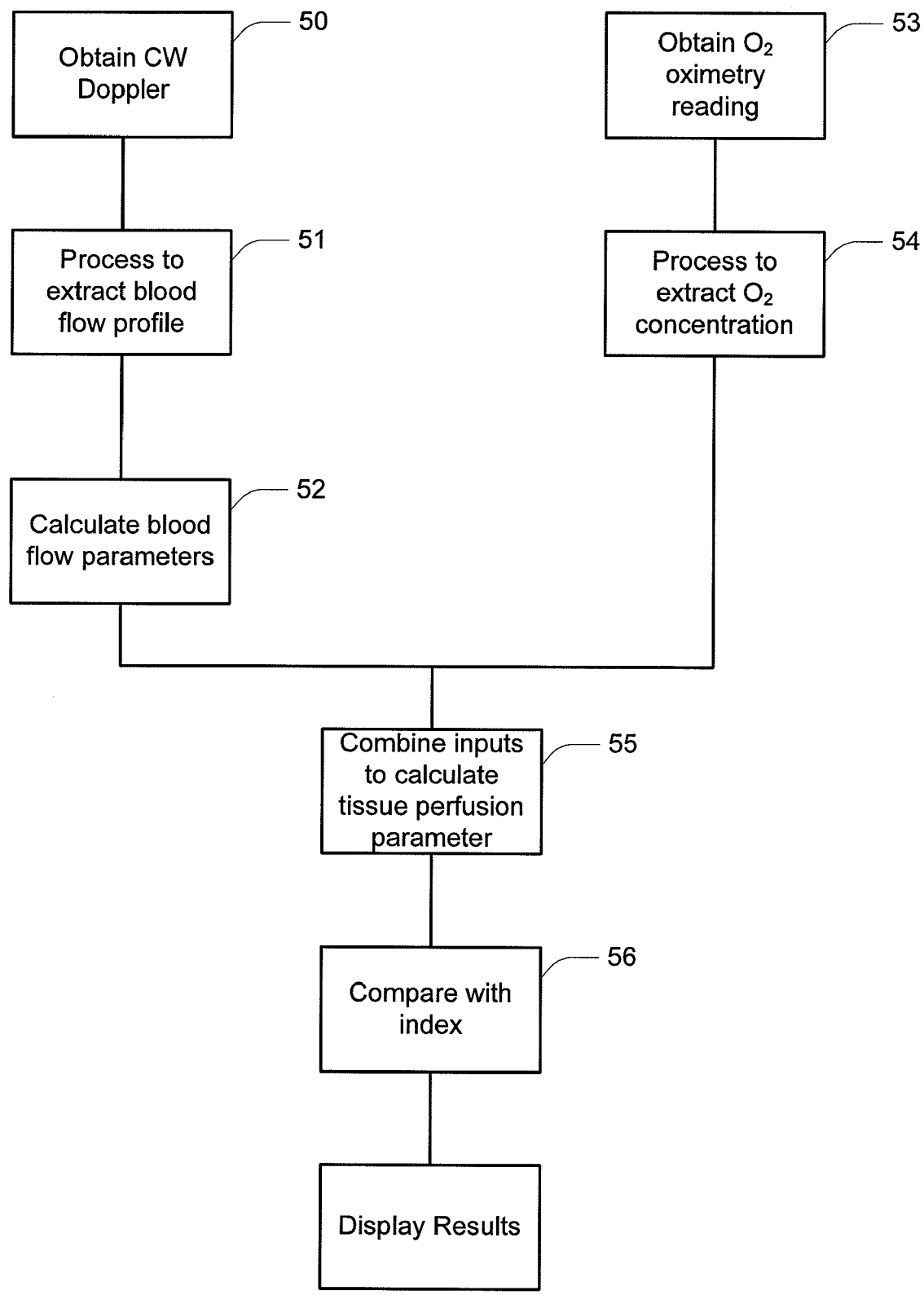
FIG. 5 is a flow diagram of the steps for producing a tissue perfusion reading.

In FIG. 5 there is illustrated the steps undertaken in producing a tissue perfusion reading. At step 50, a CW Doppler transducer reading is obtained which is then signal processed 51 in a known manner to obtain the blood flow profile. The blood flow profile is further processed 52 to extract blood flow parameters such as time velocity integral, heart rate etc to be used as inputs for a tissue perfusion parameter calculation.

Simultaneously, an output is obtained 53 from an oximetry device and processed 54 to calculate a blood oxygen concentration value. At step 55, the blood flow parameters and blood oxygen concentration are mathematically combined using the formula previously discussed to calculate a tissue perfusion parameter. The calculated tissue perfusion value can be compared with an index value 56 to determine whether a patient has a particular condition.

In order to establish the index, the steps 50-55 may be repeated on a plurality of patients and the total set of results statistically combined, e.g. averaged for patient variables such as age, sex, weight etc.

While the embodiments described relate to combined intra cardiac or aortic flow and peripheral (digital) oximetry, it is further possible to combine any vessel flow with vascular oxygen concentration to determine a tissue perfusion parameter in a relevant are of the body. Other examples include such that femoral flow could be combined with pedal oximetry, cubital or axillary flow with digital oximetry or cartoid flow could be combined with aural lobar oximetry to evaluate cerebral flow. Such devices have multiple diagnostic applications in safe and cost effective delivery of health care to humans and animals, particularly in the emergency room, operating theatre, paediatric surgery, sleep medicine and in the management of heart failure.

Additionally, the invention as described herein can be used to improve understanding of the normal physiology and pathophysiology associated with cardiovascular function, exercise and pulmonary function.

The foregoing describes embodiments of the present invention and modifications, obvious to those skilled in the art can be made thereto, without departing from the scope of the present invention.

The invention claimed is:

1. An apparatus for measuring physiologic tissue perfusion information including:
   a first device utilizing a CW Doppler monitoring method to image cardiac output from the heart to produce a first output indicative of real time blood flow of a patient;
   a second device producing a second output indicative of oxygen content of the blood; and
   a processor combining said first and said second outputs to produce a third output indicative of tissue perfusion.

2. An apparatus according to claim 1 wherein said second device uses oximetry to measure oxygen content.

3. An apparatus according to claim 1 wherein said third output is indicative of at least one of percent distance stroke saturation, percent minute distance saturation output, percent stroke volume saturation stroke volume and percent output saturation output.

4. An apparatus according to claim 1 wherein said apparatus combines intra cardiac or aortic blood flow with peripheral oximetry.

5. A method of measuring physiologic tissue perfusion information including obtaining a measurement of blood flow of a patient utilizing a CW Doppler monitoring method to image cardiac output from the heart and a measurement of real time blood oxygen content, and combining said measurements to produce an output indicative of tissue perfusion.

6. A method of creating a tissue perfusion index including:
   (a) obtaining a measurement of blood flow utilizing a CW Doppler monitoring method to image cardiac output from the heart and a measurement of real time blood oxygen content from a patient;
   (b) combining said measurements to calculate a parameter indicative of tissue perfusion in said patient;
   (c) repeating steps (a) and (b) on a plurality of patients to obtain a set of calculations of said parameter for said plurality of patients;
   (d) processing the set of calculated parameters to obtain a statistically averaged index of said parameter for a population.

7. A method of creating a tissue perfusion index for healthy population including:
   (a) obtaining a measurement of blood flow utilizing a CW Doppler monitoring method to image cardiac output from the heart and a measurement of real time blood oxygen content from a healthy patient;
   (b) combining said measurements to calculate a parameter indicative of tissue perfusion in said healthy patient;
   (c) repeating steps (a) and (b) on a plurality of healthy patients to obtain a set of calculations of said parameter for said plurality of patients;
   (d) processing the set of calculated parameters to obtain a statistically averaged index of said parameter for a healthy population.

8. A method of creating a tissue perfusion index for a population with a known condition including:
   (a) obtaining a measurement of blood flow utilizing a CW Doppler monitoring method to image cardiac output from the heart and a measurement of real time blood oxygen content from a patient with said known condition;

(b) combining said measurements to calculate a parameter indicative of tissue perfusion in said patient;
(c) repeating steps (a) and (b) on a plurality of patients with said known condition to obtain a set of calculations of said parameter for said plurality of patients;
(d) processing the set of calculated parameters to obtain a statistically averaged index of said parameter for a population with said known condition.

9. A method of diagnosing a condition in a patient including
(a) obtaining a measurement of blood flow utilizing a CW Doppler monitoring method to image cardiac output from the heart to produce and a measurement of real time blood oxygen content from a patient;
(b) combining said measurements to calculate a parameter indicative of tissue perfusion in said patient;
(c) comparing said calculated parameter with a statistically averaged index of said parameter to determine the extent to which said condition exists within said patient.

10. A method according to claim 6 wherein said parameter indicative of tissue pervasion is at least one of percent distance stroke saturation, percent minute distance saturation output, percent stroke volume saturation stroke volume and percent output saturation output.

11. A method according to claim 6 wherein said measurement of blood flow comprises a transcutaneous measure of the volume of blood flow out of a patient's heart.

12. A method according to claim 7 wherein said parameter indicative of tissue perfusion is at least one of percent distance stroke saturation, percent minute distance saturation output, percent stroke volume saturation stroke volume and percent output saturation output.

13. A method according to claim 8 wherein said parameter indicative of tissue perfusion is at least one of percent distance stroke saturation, percent minute distance saturation output, percent stroke volume saturation stroke volume and percent output saturation output.

14. A method according to claim 9 wherein said parameter indicative of tissue perfusion is at least one of percent distance stroke saturation percent minute distance saturation output, percent stroke volume saturation stroke volume and percent output saturation output.

15. A method according to claim 7 wherein said measurement of blood flow comprises a transcutaneous measure of the volume of blood flow out of a patient's heart.

16. A method according to claim 8 wherein said measurement of blood flow comprises a transcutaneous measure of the volume of blood flow out of a patient's heart.

17. A method according to claim 9 wherein said measurement of blood flow comprises a transcutaneous measure of the volume of blood flow out of a patient's heart.

* * * * *